US012751920B2

(12) United States Patent
Gupta

(10) Patent No.: US 12,751,920 B2
(45) Date of Patent: Oct. 6, 2026

(54) METHODS OF PREPARATION OF PAN TLR ANTAGONISTIC LIPOSOMAL-LNP FORMULATIONS AND USES THEREOF

(71) Applicant: Celestial Therapeutics Inc., Irvine, CA (US)

(72) Inventor: Ajay Gupta, Irvine, CA (US)

(73) Assignee: Celestial Therapeutics, Inc., Irvine, CA (US)

( * ) Notice: Subject to any disclaimer, the term of this patent is extended or adjusted under 35 U.S.C. 154(b) by 213 days.

(21) Appl. No.: 18/387,453

(22) Filed: Nov. 6, 2023

(65) Prior Publication Data

US 2024/0156733 A1 May 16, 2024

Related U.S. Application Data

(60) Provisional application No. 63/422,953, filed on Nov. 5, 2022.

(51) Int. Cl.
*A61K 9/1271* (2025.01)
*A61K 48/00* (2006.01)
*B82Y 5/00* (2011.01)
*C07K 14/705* (2006.01)

(52) U.S. Cl.
CPC .......... *A61K 9/1271* (2013.01); *A61K 48/005* (2013.01); *A61K 48/0091* (2013.01); *C07K 14/705* (2013.01); *B82Y 5/00* (2013.01)

(58) Field of Classification Search
None
See application file for complete search history.

(56) References Cited

U.S. PATENT DOCUMENTS 10,736,957 B2 8/2020 Chan et al.
2014/0348900 A1* 11/2014 Zhu .......................... A61P 25/04 422/243
2018/0125952 A1 5/2018 Fotin-Mleczek et al.
2018/0243230 A1* 8/2018 Smith .................. A61K 9/5176
2020/0009165 A1* 1/2020 Voelker ................ A61K 31/683
2020/0030432 A1* 1/2020 Ciaramella ............. A61P 31/16
2020/0306191 A1* 10/2020 Schariter ................ A61K 47/60

FOREIGN PATENT DOCUMENTS

WO WO 2021/123332 6/2021
WO WO 2023/076704 5/2023

OTHER PUBLICATIONS

Melissa P. Lokugamage et al. "Mild Innate Immune Activation Overrides Efficient Nanoparticle-Mediated RNA Delivery." Advanced Materials, vol. 32, 2020, pp. 1-9 and 25 supplemental pages. (Year: 2020).*
Annie-Louise Robson et al. "Advantages and Limitations of Current Imaging Techniques for Characterizing Liposome Morphology." Frontiers in Pharmacology, vol. 9, Article 80, Feb. 2018, pp. 1-8. (Year: 2018).*

(Continued)

*Primary Examiner* — Isaac Shomer
(74) *Attorney, Agent, or Firm* — Sheridan Ross P.C.

(57) ABSTRACT

A lipid nanoparticle (LNP) composition is provided. The composition includes a messenger RNA (mRNA) molecule; a lipid carrier system; and a toll-like receptor (TLR) antagonist.

9 Claims, 6 Drawing Sheets

(56) References Cited

OTHER PUBLICATIONS

Linde Schoenmaker et al. "mRNA-lipid nanoparticle COVID-19 vaccines: Structure and stability." International Journal of Pharmaceutics, vol. 601, 2021, Article 120586, pp. 1-13. (Year: 2021).*
Rumaina Tenchov et al. "Lipid Nanoparticles-From Liposomes to mRNA Vaccine Delivery, a Landscape of Research Diversity and Advancement." ACS Nano, vol. 15, 2021, pp. 16982-17015 and supplemental pp. 1-10. (Year: 2021).*
Tatiana M. Domingues et al. "Revealing the Lytic Mechanism of the Antimicrobial Peptide Gomesin by Observing Giant Unilamellar Vesicles." Langmuir, vol. 26(13), 2010, pp. 11077-11084. (Year: 2010).*
Debbie L. Iden and Theresa M. Allen. "In vitro and in vivo comparison of immunoliposomes made by conventional coupling techniques with those made by a new post-insertion approach." Biochimica et Biophysica Acta, vol. 1513, 2001, pp. 207-216 (Year: 2001).*
JN Israelachvili, S Marcelja, and RG Horn. "Physical principles of membrane organization." Quarterly Reviews of Biophysics, vol. 13(2), 1980, pp. 121-200. (Year: 1980).*
Yulia Eygeris et al. "Chemistry of Lipid Nanoparticles for RNA Delivery." Accounts of Chemical Research, vol. 55, 2022, published Dec. 1, 2021, pp. 2-12. (Year: 2021).*
Im Hafez et al. "On the mechanism whereby cationic lipids promote intracellular delivery of polynucleic acids." Gene Therapy, vol. 8, 2001, pp. 1188-1196. (Year: 2001).*
Kahvejian et al. "Mammalian poly(A)-binding protein is a eukaryotic translation initiation factor, which acts via multiple mechanisms," Genes & Development, 2005, vol. 19, pp. 104-113.
Kariko et al. "Suppression of RNA Recognition by Toll-like Receptors: The Impact of Nucleoside Modification and the Evolutionary Origin of RNA," Immunity, Aug. 2005, vol. 23, No. 2, pp. 165-175.
Xu "mRNA Vaccine Era—Mechanisms, Drug Platform and Clinical Prospection," International Journal of Molecular Sciences, 2020, vol. 21, No. 18, Article 6582, 35 pages.

* cited by examiner

| | | | |
|---|---|---|---|
| Sample Name: | 1 | | |
| SOP Name: | mansettings.nano | | |
| File Name: | 23.8.31 TV.dts | Dispersant Name: | PBS 1X |
| Record Number: | 7 | Dispersant RI: | 1.333 |
| Material RI: | 1.46 | Viscosity (cP): | 0.9330 |
| Material Absorbtion: | 0.000 | Measurement Date and Time: | Thursday, August 31, 2023 1:47:49 |

| | | | |
|---|---|---|---|
| Temperature (°C): | 25.0 | Duration Used (s): | 60 |
| Count Rate (kcps): | 291.9 | Measurement Position (mm): | 4.65 |
| Cell Description: | Disposable sizing cuvette | Attenuator: | 11 |

| | | | | | |
|---|---|---|---|---|---|
| | | | Size (d.nm): | % Intensity: | St Dev (d.nm): |
| Z-Average (d.nm): | 83.36 | Peak 1: | 92.07 | 98.2 | 37.25 |
| PdI: | 0.285 | Peak 2: | 5378 | 1.8 | 325.2 |
| Intercept: | 0.968 | Peak 3: | 0.000 | 0.0 | 0.000 |
| Result quality : | Good | | | | |

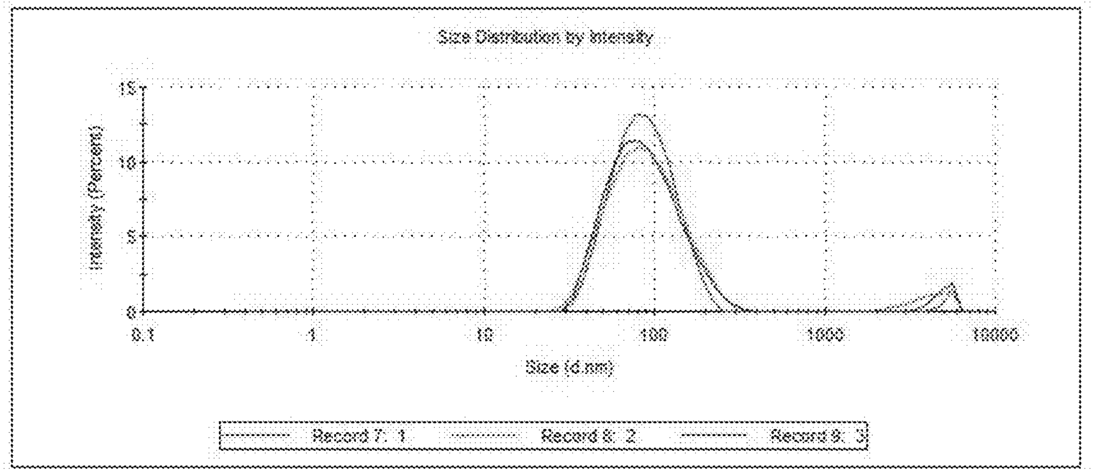

*FIG. 4*

| | | | |
|---|---|---|---|
| Sample Name: | 1 | | |
| SOP Name: | mansettings.nano | | |
| File Name: | 23.8.31 TV.dts | Dispersant Name: | PBS 1X |
| Record Number: | 4 | Dispersant RI: | 1.333 |
| Material RI: | 1.46 | Viscosity (cP): | 0.9330 |
| Material Absorbtion: | 0.000 | Measurement Date and Time: | Thursday, August 31, 2023 1:38:24 |

| | | | |
|---|---|---|---|
| Temperature (°C): | 25.0 | Duration Used (s): | 50 |
| Count Rate (kcps): | 497.9 | Measurement Position (mm): | 4.65 |
| Cell Description: | Disposable sizing cuvette | Attenuator: | 11 |

| | | | Size (d.nm): | % Intensity: | St Dev (d.nm): |
|---|---|---|---|---|---|
| Z-Average (d.nm): | 81.41 | Peak 1: | 93.09 | 95.7 | 44.75 |
| Pdl: | 0.284 | Peak 2: | 4693 | 4.3 | 786.6 |
| Intercept: | 0.954 | Peak 3: | 0.000 | 0.0 | 0.000 |
| Result quality : | Good | | | | |

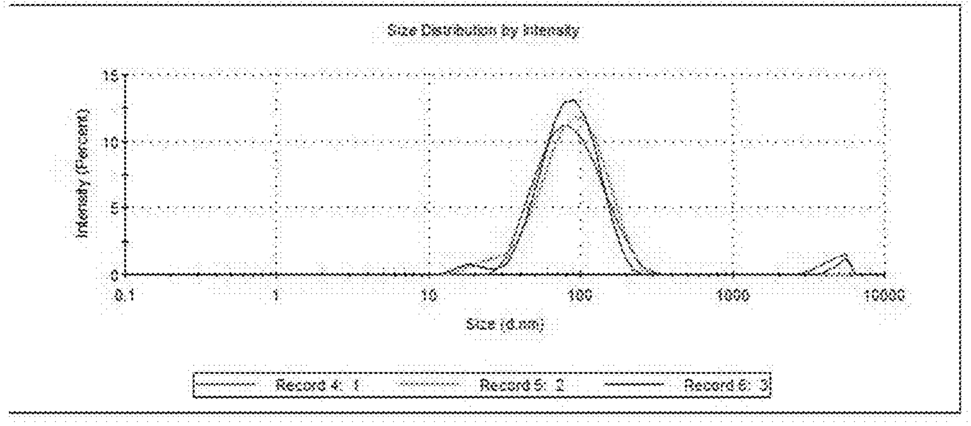

*FIG. 5*

METHODS OF PREPARATION OF PAN TLR ANTAGONISTIC LIPOSOMAL-LNP FORMULATIONS AND USES THEREOF

CROSS-REFERENCE TO RELATED APPLICATION

This application claims the benefit of priority from U.S. Provisional Patent Application No. 63/422,953, which was filed on Nov. 5, 2022, which has the same title and inventors, and which is incorporated herein by reference in its entirety.

FIELD OF THE DISCLOSURE

The present disclosure relates generally to liposomal-LNP formulations, and more particularly to liposomal-LNP formulations which exhibit antagonism to multiple TLRs.

BACKGROUND OF THE DISCLOSURE

The World Health Organization (WHO) declared the COVID-19 outbreak to be a pandemic on Jan. 30, 2020. Nine months later, there were more than 629 million cases of COVID-19 and the disease had resulted in 6.58 million confirmed deaths, making it one of the deadliest pandemics in history. COVID-19 vaccines, highlighted by the Pfizer/BionTech and Moderna SARS-CoV-2 mRNA vaccines, became readily available by December, 2020, and are credited with preventing an additional 14.4 to 19.8 million deaths in the ensuing year.

The success of the Pfizer/BionTech and Moderna SARS-CoV-2 mRNA vaccines spawned the development of a number of other mRNA vaccines and therapeutics for a variety of diseases, including infectious diseases, cancers, rare diseases and genetic diseases. These vaccines and therapeutics require mRNA to be encapsulated into lipid nanoparticles (LNP) for effective intracellular delivery, mRNA stability, endosomal escape of mRNA, efficient protein translation and robust immunogenic response.

SUMMARY OF THE DISCLOSURE

In one aspect, a lipid nanoparticle (LNP) composition is provided which comprises a messenger RNA (mRNA) molecule; a lipid carrier system; and a toll-like receptor (TLR) antagonist.

In another aspect, a method for preparing an LNP composition is provided which comprises forming liposomes; preparing an LNP formulation comprising an mRNA molecule; and generating a liposome-LNP formulation by incorporating the liposomes into the LNP formulation.

In another aspect, a composition is provided which comprises a liposome; and a lipid nanoparticle (LNP); wherein said liposome is a broad spectrum toll-like receptor (TLR) antagonist.

In another aspect, a method is provided for making a composition. The method comprises forming a providing a mixture of mRNA and a lipid nanoparticle (LNP); and adding a phospholipid to the mixture at an mRNA:phospholipid ratio within the range of 1000:1 to 1:1000 on a wt/wt or mole/mole basis.

In a further aspect, a method is provided for making a composition. The method comprises preparing a liposomal formulation of a broad spectrum toll-like receptor (TLR) antagonist; and adding the liposomal formulation to an LNP-based mRNA formulation such that the ratio of the liposome to the LNP is within the range of 1000:1 to 1:1000 on a v/v or w/w basis.

In still another aspect, a method for treating or preventing an infection or treating a cancer or a rare disease. The method comprises determining that a subject is suffering from a rare disease or cancer or has contracted, or is in danger of contracting, an infection; and administering to the subject any of the foregoing compositions, or compositions made in accordance with the foregoing methods.

BRIEF DESCRIPTION OF THE DRAWINGS

FIGS. 4-6 are graphs of particle size distribution by intensity for 0.5 μg DOTAP with 0, 10 and 100 μg CT-02, respectively.

DETAILED DESCRIPTION

The mRNA vaccines and therapeutics encapsulated into LNPs offer varying degrees of protection and side effects. Inflammation caused by mRNAs containing unmodified nucleosides via TLR 3, 7, and 8 agonism can be overcome by use of modified nucleosides such as pseudouridine [Karikó, K., Buckstein, M., Ni, H. & Weissman, D. Suppression of RNA Recognition by Toll-like Receptors. The Impact of Nuclide Modification and the Evolutionary Origin of RNA Immunity 23., 165-175 (2005)]. However, the LNPs used in nucleoside-modified mRNA vaccines and therapeutics still show high degrees of inflammation in animals and humans. Ndeupen et al. [Ndeupten, S. et al. The mRNA-LNP platform's lipid nanoparticle component used in preclinical vaccine studies is highly inflammatory. iScience 24, 2021)] have demonstrated that both cationic and ionizable lipids in LNPs can cause TLR agonism and lead to hyperinflammation, thus contributing to side effects from mRNA vaccines and therapeutics.

It has now been found that the foregoing problem may be addressed through the provision of a suitable TLR antagonist (and preferably, a broad spectrum TLR antagonist) such as, for example, palmitoyloleoylphosphatidylglycerol (POPG). The TLR antagonist may be added to LNP formulations to impart a significant reduction in inflammation, thus providing a means to achieve safer mRNA vaccines and therapeutics.

Figure 1:
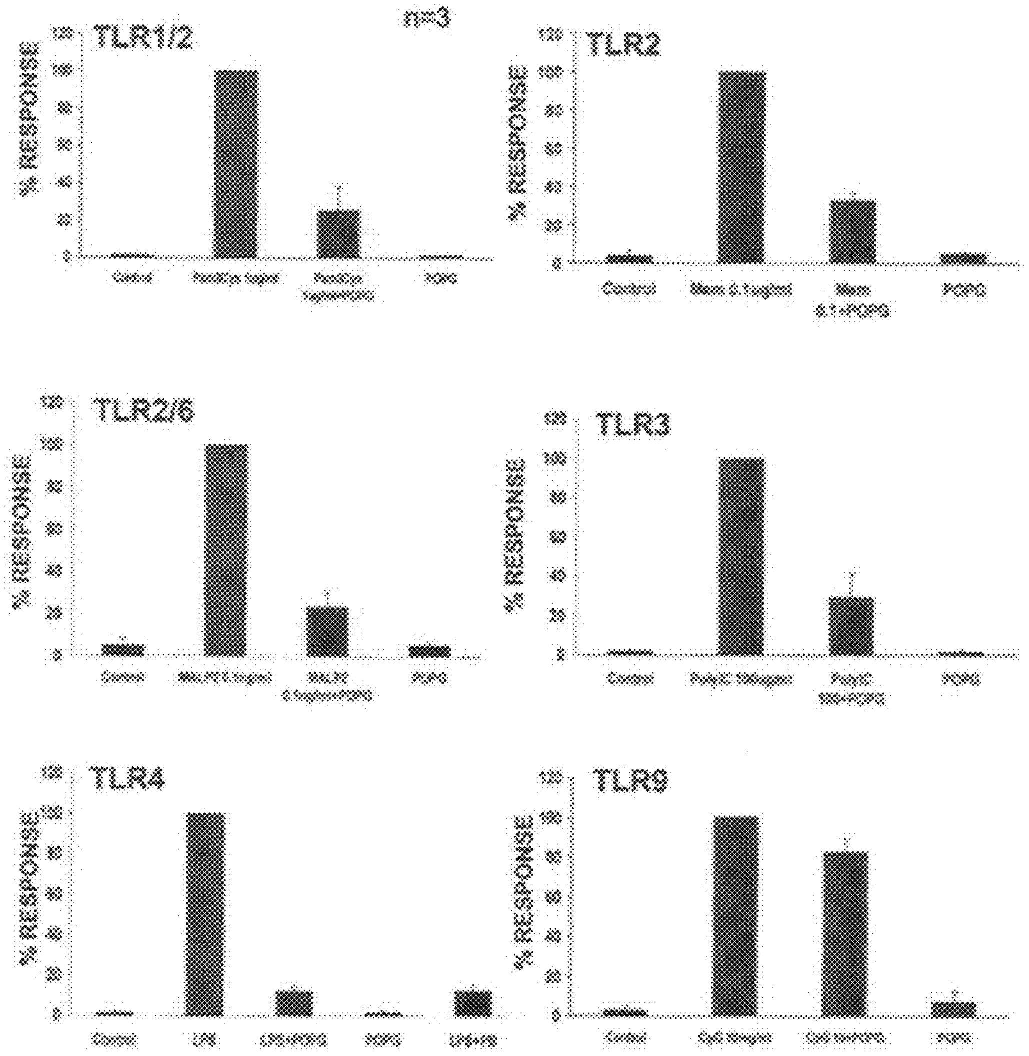
FIG. 1 is a graph showing TNFα production with TLR agonists and POPG mediated respective TLR inhibition reduces TNFα production in RAW264.7 murine macrophage cells after 24 h of POPG treatment.

The endogenous pulmonary surfactant phospholipid POPG has been shown to preferentially bind to MD-2 and CD14 and prevent their association with TLR-4 [Voelker D. R & Numata, M. Phospholipid regulation of innate immunity and respiratory viral infection. The Journal of Biological Chemistry 294, 4282 (219); Numata, M. & Voelker, D. R. Anti-inflammatory and anti-viral actions of anionic pulmonary surfactant phospholipids. Biochimica et Biophysica Acta (BBA)—Molecular and CEll Biology of Lipids 1867, 159139 (2022) Mueller, M., Brandenburg, K., Dedrick, R., Schromm, A. B. & Seydel, U. Phospholipids Inhibit Lipopolysaccharide (LPS)-Induced Cell Activation: A Role for LPS-Binding Protein. The Journal of Immunology 174, 1091-1096 (2005); K, K. et al. Anionic pulmonary surfactact phospholipids inhibit inflammatory response from alveolar macrophages and U937 cells by binding the lipopolysaccharide-interacting proteins CD14 and MD-2. J Biol Chem 284, 25488-25500 (2009)]. MD-2 and CD14 are molecular components that are responsible for facilitating the downstream intracellular signaling of TLR4 mediated inflammation. POPG binding to MD-2 and CD-14 will disrupt the downstream TLR signaling and prevent the inflammatory response [Berger, M. de Boer, J. D, van der Poll, T., Sterk, P. J. & van der Zee, J. S. Local coagulation activation following bronchial instillation of house dust mite allergen (HDM) and HDM/Lipopolysaccharide (LPS) in mild asthmatics. European Respiratory Journal 40. (2012)]. Further, POPG also exhibits considerable antagonistic activity towards other TLRs and exhibits nonidentical mechanisms of interaction with the innate immune system that result in the suppression of inflammation mediated by TNFα (see FIG. 1) and IL8 (data not shown).

LNP compositions containing TLR antagonists may be prepared in a variety of ways, and the resulting compositions may be utilized to treat a variety of diseases. One preferred (though non-limiting) embodiment for preparing such stable and efficient pan TLR antagonistic liposomal-LNP formulations involves the steps of generating POPG liposomes, preparing LNP formulations, and generating liposome-LNP formulations from the POPG liposomes and the LNP formulations.

Example 1

This example illustrates a preferred, nonlimiting example of a method for preparing POPG liposomes.

A stock lipid solution in chloroform was briefly warmed in a fumehood to redissolve any precipite that has formed. The lipid solution was then subjected to vortexing. A Hamilton syringe was washed with chloroform at least 10 times and used to transfer 150 ul of lipid solution to each of a series of test tubes (lipids original stock concentration:10 mg/ml). The chloroform was evaporated from the lipid solution completely under a nitrogen stream. Sufficient methanol was added to each test tube to cover the lipid precipitate in the test tube (usually ~50 ul to 100 ul), and the methanol was evaporated under a stream of nitrogen.

Sterile PBS (Cell Culture grade, pH 7.4; source: Sigma Aldrich, without Ca and Mg) was added to each test tube such that the final concentration was 100 mg/ml. The solution was then vortexed well, after which the test tube was sealed tightly with a double layer of parafilm. The lipids were then hydrated in a water bath for 1 hour (37° C.). The outsides of the test tubes were wiped with 70% ethanol and vortexed again to mix lipids into PBS.

A portion (150 ul) of the lipids mixture in PBS was pipeted into new LPS free eppendorf tubes. The mixture was sonicated for 20-60 minutes or until the solution becomes clear. The solution was kept chilled in the sonicator through the addition of ice. The test tubes were checked every 10-15 minutes. The test tubes were then wiped on the outside with 70% ethanol. Sterilize lipids were filtered with a 1 ml syringe using 0.22 micron filters, 0.25 gauge needles and a syringe filter as needed. About 0.5 ml of air was taken up before the lipid in order to push all the liquid out.

Example 2

This example illustrates a preferred, nonlimiting example of a method for preparing LNP formulations.

A volume of ionizable lipid mixture with the desired composition in ethanol was rapidly mixed with 3 volumes of mRNA in acetate buffer pH 4 at ionizable lipid to mRNA charge ratio 4~6 using a microfluidic Spark NanoAssmblr™ instrument. The ethanol and acetate buffer in the formed mRNA LNP were immediately dialyzed against PBS after 4-6 buffer exchanges over 4-6 h. LNPs were transferred onto a glow-discharged ultrathin carbon-coated copper grid and then blotted with filter paper before plunging into liquid ethane using the Vitrobot Mark IV. The frozen grids were loaded into a Talos transmission electron microscope equipped with a field emission gun operated at 200 kV. Images were recorded on a direct electron detector (ED20) at a total electron dose of ~50e−/Å2.

Example 3

This example illustrates a first, nonlimiting example of a method for generating liposome-LNP formulations by incorporating POPG into LNP formulations.

POPG is added to the mRNA-LNP matrix at different POPG to mRNA ratios varying from 1000:1 to 1:1000 mRNA:POPG on a wt/wt or mole/mole basis. The POPG concentration to be incorporated is optimized by studying the supramolecular assembly using techniques such as cryo-electron microscopy, which enables visualization of macromolecular structures at near-atomic resolution. The POPG:mRNA concentration is optimized so that the mRNA/LNP structure is undisrupted.

Example 4

This example illustrates a second, nonlimiting example of a method for generating liposome-LNP formulations by incorporating POPG into LNP formulations.

The liposomal formulations of the TLR antagonist (TLRA) such as POPG may be prepared separately and added in various ratios to the LNP based mRNA formulations. The ratio of liposome to the LNP may range from 1000:1 to 1:1000 Liposome:LNP on a v/v or wt/wt basis, and the concentration of the TLRA in the liposomal formulation may vary from 1 ng/ml to 100 mg/ml.

The liposome-LNP formulations made in accordance with the teachings herein may be characterized in various ways. Particle size, polydispersity index, and zeta potential of these particles may be recorded by, for example, using the Malvern zeta sizer after suspending LNPs in deionized water at pH 4.0 and 7.4. The encapsulation efficiency may be studied using Ribogreen, during which the fluorescence of Ribogreen at Ex485/Em528 may be recorded. The encapsulation efficiency (EE %):EE (%)=(1−free mRNA concentration/total mRNA concentration)×100.

Further aspects of the compositions and methodologies disclosed herein may be appreciated with respect to the following additional, non-limiting examples. These examples illustrate a method for improving an mRNA vaccine platform technology by incorporating specific pattern receptor agonism and pan TLR antagonism using Chikungunya as a model pathogen.

Example 5

This example illustrates the CT-02 dose response for optimal GFP mRNA transfection in-vitro.

Figure 2:
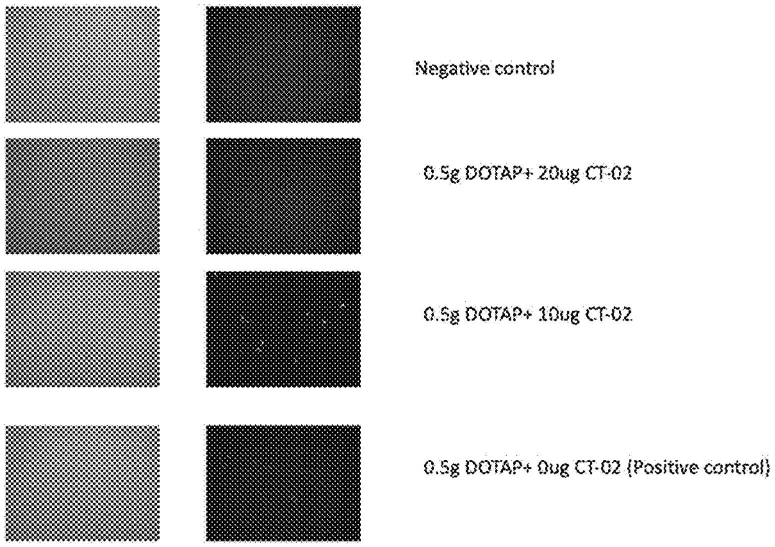
FIG. 2 depicts the results of a study undertaken to determine an optimal concentration of CT-02 that produces robust transfection of mRNA. The results depicted show GFP mRNA Transfection as a function of CT-02 concentration.
Figure 3:
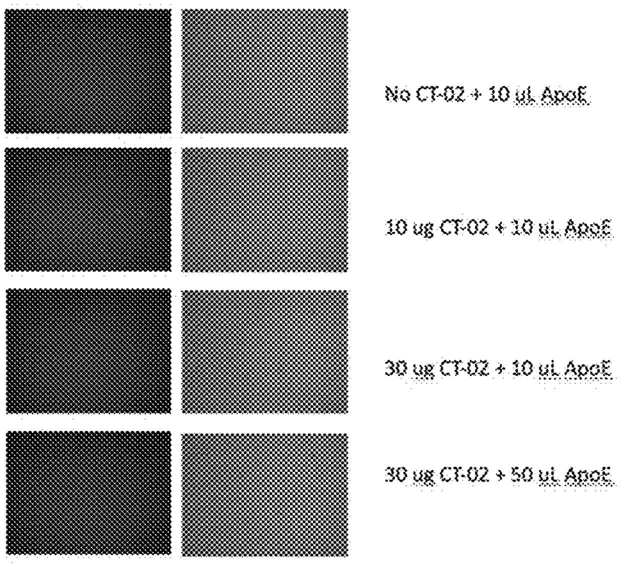
FIG. 3 depicts the impact of ApoE on GFP-mRNA transfection as a function of CT-02 concentration.

It is desirable to define a formulation of CT-02 that suppresses the immune response and retains efficient mRNA transfection and exogenous gene expression with a mRNA- LNP delivery. In order to do so, CT-02 liposomes were mixed with mRNA-LNP prior to delivery of cells. In this example, an optimal concentration of CT-02 that produces robust transfection of mRNA was determined. It was found that concentrations of CT-02>20 μg/ml would inhibit mRNA-LNP transfection efficiency (see FIG. 2).

Example 6

A dose de-escalation study was performed where CT-02 in PBS formulation was mixed with mRNA-LNP at varying concentrations ranging from 0-400 μg/ml and transfection efficiency was determined on 293T cells.

To this end, mRNA encoding for GFP was acquired from TriLink. The mRNA was encapsulated into a lipid nanoparticle using the Precision Nanosystems Ignite instrument. LNP consisted of DOTAP:DSPC:Cholesterol:PEG2000 at the ratio of 50:10:38.5:1.5. Here, DOTAP refers to 18:1 TAP, 1,2-dioleoyl-3-trimethylammonium-propane (chloride salt), which is used for the preparation of cationic liposome and liposome-DNA complexes. DOTAP is a cationic liposome-forming compound used for transfection of DNA, RNA, and other negatively charged molecules into eukaryotic cells.

CT-02 dry powder was generated by gentle evaporation of the chloroform solution followed by dissolution in methanol and subsequent methanol evaporation under a gently stream of dry nitrogen. The resulting CT-02 dry film was suspended as a liposomal solution in PBS solution. Briefly, PBS was added to CT-02 residue at a concentration of 200 mg/ml. Samples were incubated in a water bath for 1 hour at 37° C. The solution was then sonicated until CT-02 went from precipitate to homogenous opaque solution. This solution was then added to a monolayer of 293T cells at varying concentrations from 0-400 μg/ml in a 24 well plate. 0.5 μg of GFP mRNA LNP was added to the cells. 24 hours later, cells were imaged on a Keyonce inverted imaging microscope and GFP expression was qualitatively determined. In these assays, GFP expression is a proxy for mRNA-LNP transfection efficiency.

CT-02 at concentrations greater than or equal to 20 μg/ml inhibited mRNA LNP transfection as evidenced by loss of GFP expression. All samples with 10 μg/ml or less of CT-02 had equivalent GFP expression compared to the negative control without any CT-02.

Two plausible mechanisms of inhibition of mRNA transfection by high doses of CT-02 were considered, including (1) a physical disruption of the LNPs encapsulating mRNA by CT-02 liposomes; (2) interaction of ApoE with CT-02 leading to an inhibition of mRNA-LNP cellular uptake. The experiments in the following examples were undertaken to determine which (if either) of these mechanisms may be at play.

Example 7

Regarding CT-02-ApoE interaction, uptake of the mRNA-LNP particle inside cells is mediated by the LDL receptor on cell surface. Upon injection into the host, the mRNA-LNP is bound by host ApoE. ApoE is a ubiquitous protein that binds lipid complexes and mediates cell uptake. ApoE interacts with the LDL receptor on the cell surface to trigger endocytosis.

In in vitro studies, it was observed that high concentrations of CT-02 inhibited mRNA-LNP transfection. It was thus hypothesized that CT-02 is binding to ApoE and inhibiting LNP-ApoE interactions. In order to test this hypothesis, the concentration of ApoE in an in vitro mRNA-LNP transfection assay was increased and mRNA-LNP transfection efficiency was quantified.

Figure 6:
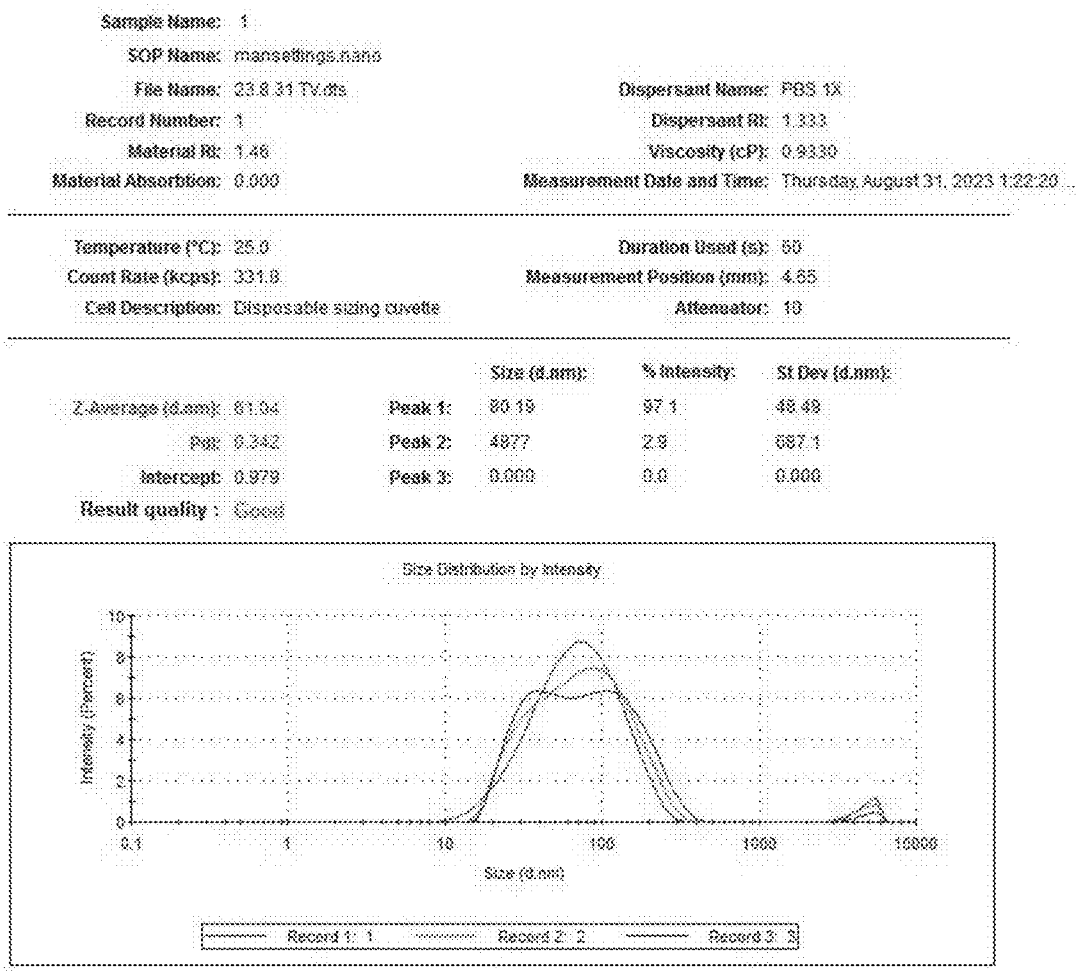

To this end, 293T cells were plated in a monolayer on a 24-well plate. CT-02 liposomes in PBS were added to the 293T cells at concentrations of 10 μg/ml or 30 μg/ml. 10 μl or 50 μl of ApoE was then added to the cells and then 0.5 μg of GFP mRNA-LNP. It was observed that 30 μg of CT-02+10 μl of ApoE inhibited GFP expression as expected. Increasing the ApoE 5-fold did not rescue GFP expression (see FIG. 6). Since increasing the concentration of ApoE had no effect on GFP mRNA transfection efficiency in the presence of 30 μg/ml CT-02, it thus follows that CT-02 binding to ApoE is not hindering mRNA-transfection efficiency, thus negating that hypothesis.

Example 8

This example investigated the effect of CT-02 on LNP particle stability.

Given that high concentration of CT-02 inhibited mRNA-LNP transfection efficiency, the decision was made to determine whether CT-02 liposomes destabilize the mRNA-LNP. In this experiment, mRNA-LNP was incubated with CT-02 liposomes and quantified particle size and heterogeneity. To this end, GFP mRNA LNP was mixed with CT-02 at 10 or 100 μg/ml (FIGS. 5 and 6, respectively; the case for μg/ml CT-02 is shown in FIG. 4 for reference).

LNP particles were then analyzed on a Zetasizer DLS instrument. Particle homogeneity and size are graphed. At 0 or 10 μg/ml of CT-02, LNPs were a homogenous size of 92-93 nm. At 100 μg/ml CT-02, LNP particles showed increased heterogeneity in size as well as the appearance of smaller particles of <50 nm. This shift in particle dynamics suggests that the LNP particles break down in the presence of high concentrations of CT-02 liposomes. Concentrations of 10 μg/ml CT-02 had no impact on particle dynamics, thus suggesting that this concentration of CT-02 may be suitable for some applications.

Various materials may be utilized in the compositions disclosed herein. These include, for example, the phospholipid composiotions described in U.S. 2023/0218646 (Gupta), which is incorporated herein by reference in its entirety. The compositions described herein may be incorporated into various other compositions including, for example, the antimicrobioal phospholipid compositions (and dry powders containing the same) disclosed in WO2023028354 (Gupta et al.), which is incorporated herein by reference in its entirety.

The compositions disclosed herein may be utilized to treat various diseases or indications. Thus, for example, these compositions may be utilized to treat subjects who have, or who are at risk of developing, rhinovirus infections, respiratory Syncytial virus infections, influenza infections, coronavirus infections, and inflammation. These compositions may also be utilized in various pharmaceutical compositiosn and vaccines including, for example, the vaccines disclosed in WO2023076704 (Gupta), which is incorporated herein by reference in irts entirety.

The above description of the present invention is illustrative and is not intended to be limiting. It will thus be appreciated that various additions, substitutions and modifications may be made to the above described embodiments without departing from the scope of the present invention. Accordingly, the scope of the present invention should be construed in reference to the appended claims. For convenience, some features of the claimed invention may be set forth separately in specific dependent or independent claims.

However, it is to be understood that these features may be combined in various combinations and subcombinations without departing from the scope of the present disclosure. By way of example and not of limitation, the limitations of two or more dependent claims may be combined with each other without departing from the scope of the present disclosure.

What is claimed is:

1. A method for preparing a liposome-lipid nanoparticle (LNP) formulation, the method comprising:

forming liposomes, wherein the liposomes are formed from palmitoyloleoylphosphatidylglycerol (POPG);

preparing an LNP formulation comprising an mRNA molecule;

sonicating the liposomes to achieve a desired size distribution before combining with the LNP formulation; and generating a liposome-LNP formulation by incorporating the liposomes into the LNP formulation.

2. The method of claim 1, wherein the liposomes are formed using a method comprising dissolving POPG in a solvent, evaporating the solvent, and hydrating the resultant lipid film with a buffer solution.

3. The method of claim 1, wherein the LNP formulation is prepared by a process that includes mixing an ionizable lipid with mRNA in an acidic buffer, followed by dialysis against a buffer solution.

4. The method of claim 1, wherein generating the liposome-LNP formulation by incorporating the liposomes into the LNP formulation includes mixing the liposomes with the LNP formulation using a technique that maintains the integrity of the mRNA molecule and LNPs.

5. The method of claim 1, wherein the liposomes and the LNP formulation are combined under conditions that prevent aggregation of the resultant liposome-LNP formulation.

6. The method of claim 1, wherein the final concentration of the POPG in the liposome-LNP formulation is optimized based on the inflammatory response in an in vitro or in vivo model.

7. The method of claim 1, further comprising characterizing the liposome-LNP formulation by determining its particle size, polydispersity index, and zeta potential.

8. The method of claim 1, further comprising filtering the liposome-LNP formulation through a sterilizing filter to ensure sterility of the composition.

9. The method of claim 1, wherein the mRNA molecule within the LNP formulation encodes an antigen of a pathogen or a protein of interest for gene therapy.

* * * * *